US012576170B2

(12) United States Patent
Wang et al.

(10) Patent No.: US 12,576,170 B2
(45) Date of Patent: Mar. 17, 2026

(54) RK POLYPEPTIDE RADIOPHARMACEUTICAL TARGETING HER2 AND PREPARATION METHOD THEREOF

(71) Applicant: BEIJING GILUNTIDE PHARMACEUTICAL CO., LTD., Beijing (CN)

(72) Inventors: Fan Wang, Beijing (CN); Jiyun Shi, Beijing (CN); Shuaifan Du, Beijing (CN); Bing Jia, Beijing (CN)

(73) Assignee: Beijing Giluntide Pharmaceutical Co., Ltd., Beijing (CN)

( * ) Notice: Subject to any disclaimer, the term of this patent is extended or adjusted under 35 U.S.C. 154(b) by 1033 days.

(21) Appl. No.: 17/595,751

(22) PCT Filed: May 22, 2020

(86) PCT No.: PCT/CN2020/091801
§ 371 (c)(1),
(2) Date: Nov. 23, 2021

(87) PCT Pub. No.: WO2020/238795
PCT Pub. Date: Dec. 3, 2020

(65) Prior Publication Data
US 2022/0211884 A1 Jul. 7, 2022

(30) Foreign Application Priority Data

May 24, 2019 (CN) .......................... 201910438639.0
Aug. 22, 2019 (CN) .......................... 201910778630.4

(51) Int. Cl.
*A61K 51/08* (2006.01)
*A61K 51/06* (2006.01)

(52) U.S. Cl.
CPC .......... *A61K 51/088* (2013.01); *A61K 51/065* (2013.01)

(58) Field of Classification Search
CPC ...... A61K 51/00; A61K 51/08; A61K 51/088; A61K 51/065; A61P 35/00; C07K 7/06
See application file for complete search history.

(56) References Cited

FOREIGN PATENT DOCUMENTS

| | | | | |
|---|---|---|---|---|
| CN | 101428148 A | | 5/2009 | |
| CN | 109045313 A | | 12/2018 | |
| CN | 110339375 | * | 10/2019 | |
| CN | 110339375 A | * | 10/2019 | .......... A61K 51/065 |

OTHER PUBLICATIONS

Zihua Wang et al., "Microarray Based Screening of Peptide Nano Probes for HER2 Positive Tumor", Analytical Chemistry, vol. 87, No. 16, Jul. 28, 2015, pp. 8367-8372, XP055757642, ISSN: 0003-2700, DOI: 10.1021/acs.analchem.5b01588.
Cun-Jing Jin et al., "Comparison of in Vitro and in Vivo Characteristics of 99Tom-Labeled Cyclic RGD Dimers With PEG4/2PEG4 Linkers", Journal of Nuclear and Radiochemistry, vol. 32, No. 5, Oct. 31, 2010, pp. 287-292, XP009524493.

* cited by examiner

*Primary Examiner* — D. L. Jones
(74) *Attorney, Agent, or Firm* — McCarter & English, LLP

(57) ABSTRACT

Disclosed are an rk polypeptide radiopharmaceutical targeting HER2, and a preparation method therefor. The rk polypeptide radiopharmaceutical comprises an rk polypeptide dimer and a radionuclide, wherein the radionuclide marks the rk polypeptide dimer by means of a chelating agent, the rk polypeptide dimer is a polypeptide dimer formed by connecting PKM and rk polypeptide monomers and then dimerizing two rk polypeptide monomers connected to the PKM; each rk polypeptide monomer is a D-type amino acid linear eight-membered polypeptide, and the sequence of the rk polypeptide monomer is as follows: Arg-Asn-Trp-Glu-Leu-Arg-Leu-Lys; and the PKM represents a pharmacokinetic modifying molecule. The radiopharmaceutical is used for imaging diagnosis of HER2-positive tumor patients, and medication guidance and real-time therapeutic effect monitoring of patients treated by monoclonal antibodies of the anti-cancer drug trastuzumab.

3 Claims, 19 Drawing Sheets

HER2-negative/EGFR-positive breast cancer MDA-MB-468 model

RK POLYPEPTIDE RADIOPHARMACEUTICAL TARGETING HER2 AND PREPARATION METHOD THEREOF

TECHNICAL FIELD

The present invention relates to a novel tumor diagnostic radiopharmaceutical and a method for preparing the same, and in particular, to radiographic diagnosis in an HER2-positive tumor patient and medication guidance and real-time efficacy monitoring in a patient receiving anticancer drug trastuzumab.

BACKGROUND

Breast cancer is one of the most common malignant tumors in women, comprising about 25% of the malignant tumors in women. In recent years, it demonstrates an increasing tendency in younger populations, and seriously threatens the health of women. Human epidermal growth factor receptor 2 (HER2) is a proto-oncogene. Its abnormal amplification and overexpression can lead to malignant transformation of cells, and are closely associated with infiltration, metastasis and relapse of breast cancer. In clinical cases, about 30% of breast cancer patients are HER2-positive.

Statistics suggest a high cure rate of patients with early breast cancer. However, since early symptoms of many tumors are not evident, the optimal treatment period is missed at the time of diagnosis. Whereas, molecular imaging techniques, which are capable of observation at a cellular or molecular level, have made early diagnosis of tumors possible. Among these, nuclear medicine imaging (PET, SPECT) demonstrates increasing clinical importance due to its high sensitivity, tissue penetration, capability of in vivo quantification and selection of various nuclides.

Trastuzumab, a humanized monoclonal antibody targeting HER2, is a first-line medicament for treating HER2-positive breast cancer. It can effectively improve the overall survival rate, and has showed efficacy in treatment of both early and advanced (metastatic) breast cancers. However, only a part of patients are sensitive to trastuzumab therapy. Whether receiving the antibody monotherapy or a combination therapy with other drugs, patients have showed resistance to some extent after a period of treatment. Thus, it is crucial to assess changes in HER2 expression level before and during treatment. Clinically, pathological tissues are obtained by surgery or needle biopsy for determination of HER2 expression level by IHC or FISH. However, biopsies are invasive and have problems such as a high rate of inconsistency (6%-48%) in HER2 expression levels between primary and metastatic lesions, and a small sample size necessarily representing the HER2 expression level in the entire tumor. On this basis, molecular probes capable of targeting HER2 show great advantages. Researches have demonstrated that the polypeptide of a KLRLEWNR sequence has good HER2-targeting capacity and can effectively distinguish HER2 expressions in different tumor cells. The optimized rk polypeptide pharmaceutical (rnwelrlk) disclosed herein has a D-amino acid sequence that is not recognized by proteases in vivo, and effectively improved metabolic stability in vivo, thereby improving the uptake in tumor tissues. In addition, the rk polypeptide dimer introduces a linker of sufficient length between the two polypeptides, providing a sufficient distance between the two polypeptides in the dimer for binding two HER2 targets simultaneously and a higher affinity than the monomer. Addition of PKM between the bifunctional chelating agent HYNIC for radionuclide labeling and the rk polypeptide dimer optimizes the pharmacokinetics and thus gives better diagnosis and treatment effects. It is noted that the rk polypeptide pharmaceutical binds to a different site in HER2 from trastuzumab, and thus can be used for monitoring the therapeutic effect during trastuzumab treatment without being affected by the dosage, and play a key role in precision medicine.

SUMMARY

The present invention is intended to provide a novel polypeptide radiopharmaceutical targeting an HER2-positive tumor. The purpose of the present invention is achieved by providing:

An rk polypeptide radiopharmaceutical targeting HER2, comprising an rk polypeptide dimer and a radionuclide, wherein the radionuclide labels the rk polypeptide dimer through a chelating agent, and the rk polypeptide dimer is a polypeptide dimer formed by conjugating a PKM (pharmacokinetic modifying molecule) with an rk polypeptide monomer and dimerizing two rk polypeptide monomers conjugated with the PKM; the rk polypeptide monomer is an 8-membered linear polypeptide of D-amino acids with a sequence of Arg-Asn-Trp-Glu-Leu-Arg-Leu-Lys (arginine-asparagine-tryptophan-glutamic acid-leucine-arginine-leucine-lysine, abbreviated rnwelrlk).

Further, a PKM is conjugated between the rk polypeptide dimer and the chelating agent.

Further, the PKM is polyethylene glycol ($PEG_n$) or 8-aminooctanoic acid (Aoc), and $PEG_n$ is preferably $PEG_4$, $PEG_6$, $PEG_8$ or $PEG_{12}$.

Further, the radionuclide is any one of $^{99m}Tc$, $^{68}Ga$, $^{64}Cu$, $^{111}In$, $^{90}Y$ and $^{177}Lu$.

Further, the chelating agent is any one of HYNIC, NOTA, DOTA and DTPA.

Further, the rk polypeptide radiopharmaceutical is a colorless transparent liquid injection.

The preferable scheme of the medicine is: the radionuclide is $^{99m}Tc$, the rk polypeptide is an 8-membered linear polypeptide rnwelrlk of D-amino acids; the rk polypeptide dimer is synthesized by conjugating $PEG_4$ or Aoc with the rk polypeptide monomer and dimerizing two rk polypeptide monomers conjugated with $PEG_4$ or Aoc; the radionuclide $^{99m}Tc$ labels the rk polypeptide dimer through the bifunctional chelating agent HYNIC; a pharmacokinetic modifying molecule PKM (PKM=Aoc or $PEG_4$) is conjugated between the rk polypeptide dimer and the bifunctional chelating agent; the rk polypeptide radiopharmaceutical is $^{99m}Tc$-HYNIC-PKM-$(PKM$-rk$)_2$; the rk polypeptide radiopharmaceutical is a colorless transparent liquid injection.

For synthesis of the pharmaceutical, the PKM is firstly conjugated with the polypeptide rnwelrlk of D-amino acids, and the polypeptides are dimerized, providing a sufficient distance between two polypeptides in the dimer molecule for binding two HER2 targets simultaneously, enhanced stability in vivo, and improved pharmacokinetics and targeting performance against tumor. The combination of the bivalent form can further enhance the pharmaceutical intake in tumor cells, and achieve better diagnosis effect. The radionuclide $^{99m}Tc$ is labeled on the rk polypeptide dimer molecule through the bifunctional chelating agent. The labeled pharmaceutical aggregates at a tumor lesion through the targeting capacity of the rk polypeptides in vivo, and an HER2- positive tumor can be radiographically diagnosed utilizing single-photon emission computed tomography in nuclear medicine.

A method for preparing a rk polypeptide radiopharmaceutical, comprising:

a. Preparation of HYNIC-PKM-COOH dissolving Fmoc-protected PKM-COOH in a final concentration of 20% (v/v) solution of piperidine in DMF (dimethyl formamide), reacting at room temperature for 15-30 min, adding diethyl ether to precipitate the PKM, centrifuging, discarding the supernatant, washing the precipitate with diethyl ether, and removing the residual diethyl ether to give an expected product $NH_2$-PKM-COOH; and dissolving HYNIC-NHS and $NH_2$-PKM-COOH in DMF, adding DIEA to adjust to pH 8.5-9.0, stirring overnight at room temperature, separating and purifying the crude product by YMC-Pack ODS-A semi-preparative HPLC, collecting fractions of the objective product, combining collections and lyophilizing to give the expected product HYNIC-PKM-COOH confirmed by MALDI-TOF-MS;

b. Preparation of HYNIC-PKM-OSu dissolving HYNIC-PKM-COOH in DMF, adding NHS and EDC·HCl, stirring for 5-10 hours at room temperature, adding a 50% (v/v) aqueous ACN solution with into the reaction solution, filtering, separating and purifying the filtrate by YMC-Pack ODS-A semi-preparative HPLC, collecting fractions of the objective product, combining the collections and lyophilizing to give the expected product HYNIC-PKM-OSu confirmed by MALDI-TOF-MS;

c. Preparation of (PKM-Rk-Dde)$_2$-Glu dissolving PKM-rk-Dde and OSu$_2$-Glu-Boc in DMF, adding DIEA to adjust to pH 8.5-9.0, stirring overnight at room temperature, separating and purifying the crude product by YMC-Pack ODS-A semi-preparative HPLC, collecting fractions of the objective product, combining collections and lyophilizing to give the expected product (PKM-rk-Dde)$_2$-Glu-Boc; and dissolving the lyophilized product (PKM-rk-Dde)$_2$-Glu-Boc in 1 mL of TFA, reacting for 5 min at room temperature, and purging the reaction solution with nitrogen to dryness to give the expected product (PKM-rk-Dde)$_2$-Glu confirmed by MALDI-TOF-MS; wherein rk denotes an rk polypeptide monomer;

d. Preparation of HYNIC-PKM-(PKM-Rk)$_2$ dissolving (PKM-rk-Dde)$_2$-Glu and HYNIC-PKM-OSu in DMF, adding DIEA to adjust to pH 8.5-9.0, stirring overnight at room temperature, separating and purifying the crude product by YMC-Pack ODS-A semi-preparative HPLC, collecting fractions of the objective product, combining collections and lyophilizing to give the expected product HYNIC-PKM-(PKM-rk-Dde)$_2$; and dissolving HYNIC-PKM-(PKM-rk-Dde)$_2$ in a 2% (v/v) solution of hydrazine hydrate in DMF, reacting for 30 min at room temperature, separating and purifying the crude product by YMC-Pack ODS-A semi-preparative HPLC, collecting fractions of the objective product, combining collections and lyophilizing to give the expected product HYNIC-PKM-(PKM-rk)$_2$ confirmed by MALDI-TOF-MS; and e. preparation of $^{99m}$Tc-HYNIC-PKM-(PKM-rk)$_2$ preparing a mixed solution containing trisodium triphenylphosphine-3,3',3"-trisulfonate (TPPTS), tricine, disodium succinate hexahydrate, succinic acid and HYNIC-PKM-(PKM-rk)$_2$ in a mass ratio of (4-6):(6-7):(38-39):(12-13): 0.04, and lyophilizing the mixed solution; and adding 1 mL of $Na^{99m}TcO_4$ solution to the lyophilized powder, reacting in a water bath at 100° C. for 20-25 min, and cooling at room temperature after the reaction is completed to give the rk polypeptide radiopharmaceutical. The product is analyzed by HPLC and preserved for further use.

The HPLC is performed using an Agilent 1260 HPLC system equipped with a YMC-Pack ODS-A semi-preparative column (250×10 mm, I.D. S-5 μm, 12 nm) or analytical column (250×4.6 mm, I.D. S-5 μm, 12 nm) with a gradient elution for 30 min, wherein the mobile phase A is deionized water (containing 0.05% TFA), and the mobile phase B is acetonitrile (containing 0.05% TFA). Step a: for the semi-preparative column, the flow rate is 4 mL/min and the elution gradients are 90% A and 10% B at beginning, 50% A and 50% B at 25 min, and 90% A and 10% B at 30 min. Step b: for the analytical column, the flow rate is 1 mL/min and elution gradients are 90% A and 10% B at beginning and 30% A and 70% B at 20 min.

The rk polypeptide radiopharmaceutical is used for radiographic diagnosis in HER2-positive tumor patients and medication guidance and real-time efficacy monitoring in patients receiving anticancer drug trastuzumab.

Beneficial Effects of the Present Invention

1. For the rk polypeptide radiopharmaceutical disclosed herein, the D-amino acid sequence is not recognized by proteases in vivo and can effectively improve the metabolic stability in vivo, thereby improving the uptake in tumor tissues.

2. For synthesis of the rk polypeptide radiopharmaceutical disclosed herein, four polyethylene glycol molecules (PEG$_4$) or 8-aminooctanoic acid (Aoc) is firstly conjugated with the polypeptide of D-amino acids, and the polypeptides are dimerized, providing a sufficient distance between two polypeptides in the dimer molecule for binding two HER2 targets simultaneously. The combination of the bivalent form can further enhance the pharmaceutical intake in tumor cells, and achieve better diagnosis effect.

3. The present invention not only introduces a PKM (PEG$_4$ or Aoc) between the two rk polypeptides, but also introduces a PKM between the bifunctional chelating agent HYNIC for radionuclide labeling and the rk polypeptide dimer targeting HER2, i.e., HYNIC-PKM-(PKM-rk)$_2$, thus providing improved biocompatibility and optimized pharmacokinetics for the probe, particularly the kinetics of elimination from non-tumor tissues.

4. In the present invention, HYNIC serves as the bifunctional chelating agent, and tricine and TPPTS are used as co-ligands, giving the "$^{99m}$Tc-HYNIC nucleus" better in-vivo and in-vitro stabilities.

BRIEF DESCRIPTION OF THE DRAWINGS

FIG. 2 illustrates structural schematic of $^{99m}$Tc-HYNIC-PKM-(PKM-rk)$_2$ conjugate, wherein rnw denotes the rk polypeptide.

DETAILED DESCRIPTION

Among the materials used in the embodiments of the present invention:

1-(3-Dimethylaminopropyl)-3-ethylcarbodiimide hydrochloride (EDC. HCl), N-hydroxysuccinimide (NHS), succinic acid, disodium succinate hexahydrate, trisodium triphenylphosphine-3,3',3"-trisulfonate (TPPTS), N,N-dimethylform amide (DMF), tricine were purchased from Sigma-Aldrich, USA. HYNIC-NHS (hydrazino nicotinamide) was purchased from Noca-biochem (USA). PEG$_4$-rnwelrlk and Aoc-rnwelrlk polypeptide monomers were purchased from GL Biochem (China). Na$^{99m}$TcO$_4$ eluate was purchased from HTA Co., Ltd. (China).

Figure 1:
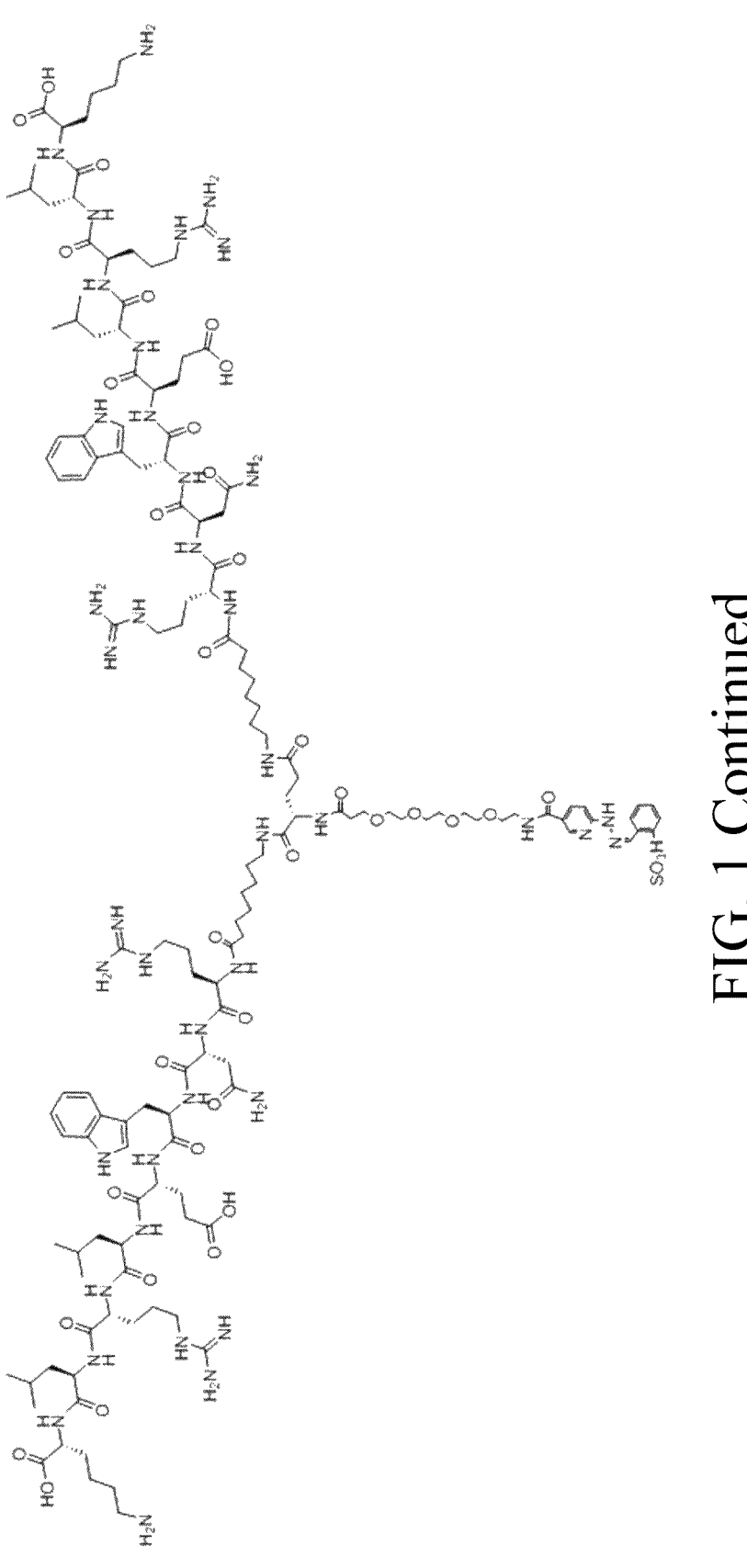
FIG. 1 illustrates structural schematics of (A) the rk polypeptide, (B) HYNIC-PEG$_4$-rk, and (C) HYNIC-PEG$_4$-(Aoc-rk)$_2$.

An rk polypeptide radiopharmaceutical targeting HER2, comprising an rk polypeptide dimer and a radionuclide, wherein the radionuclide labels the rk polypeptide dimer through a chelating agent, and the rk polypeptide dimer is a polypeptide dimer formed by conjugating a PKM (pharmacokinetic modifying molecule) with the rk polypeptide monomer and dimerizing two rk polypeptide monomers conjugated with the PKM; the rk polypeptide monomer is an 8-membered linear polypeptide of D-amino acids with a sequence of Arg-Asn-Trp-Glu-Leu-Arg-Leu-Lys (arginine-asparagine-tryptophan-glutamic acid-leucine-arginine-leucine-lysine, abbreviated rnwelrlk); the structural formula of the polypeptide is shown in FIG. 1.

A PKM is conjugated between the rk polypeptide dimer and the chelating agent. The PKM is polyethylene glycol (PEG$_n$) or 8-aminooctanoic acid (Aoc), PEG$_n$ is preferably PEG$_4$, PEG$_6$, PEG$_8$ or PEG$_{12}$. The radionuclide is any one of $^{99m}$Tc, $^{68}$Ga, $^{64}$Cu, $^{111}$In, $^{90}$Y and $^{177}$Lu. The chelating agent is any one of HYNIC, NOTA, DOTA and DTPA. The rk polypeptide radiopharmaceutical is a colorless transparent liquid injection.

The following examples are preferred rk polypeptide radiopharmaceuticals targeting HER2 and methods for preparing the same.

Example 1

This example exemplifies $^{99m}$Tc-HYNIC-PEG$_4$-(Aoc-rk)$_2$ as the polypeptide radiopharmaceutical and the method for preparing the same.

In $^{99m}$Tc-HYNIC-PEG$_4$-(Aoc-rk)$_2$, the rk polypeptide monomer is linear polypeptide rnwelrlk of D-amino acids, the rk polypeptide dimer is formed by conjugating the linker Aoc with the rk polypeptide monomer and then dimerizing two rk polypeptide monomers conjugated with Aoc, a radionuclide $^{99m}$Tc labels the rk polypeptide dimer through the bifunctional chelating agent HYNIC, and a pharmacokinetic modifying molecule PEG$_4$ is conjugated between the rk polypeptide dimer and the bifunctional chelating agent. The rk polypeptide radiopharmaceutical is $^{99m}$Tc-HYNIC-PEG$_4$-(Aoc-rk)$_2$ with its structural formula shown in FIG. 2. The rk polypeptide radiopharmaceutical is a colorless transparent liquid injection.

The method for preparing $^{99m}$Tc-HYNIC-PEG$_4$-(Aoc-rk)$_2$ comprises the following steps:

Preparation of HYNIC-PEG$_4$-COOH: Fmoc-protected PEG$_4$-COOH was dissolved in DMF, and piperidine was added to make a final concentration of 20%. The system was reacted at room temperature for 20 min, and 10 mL of diethyl ether was added at 4° C. to precipitate PEG$_4$-COOH. The mixture was centrifuged at 4000 rpm at 4° C. for 5 min and the supernatant was discarded. The precipitate was washed with diethyl ether at 4° C. for 3 times, and residual diethyl ether was removed by rotary evaporation to give NH$_2$-PEG$_4$-COOH. HYNIC-NHS and NH$_2$-PEG$_4$-COOH were dissolved in DMF. The system was adjusted to pH 8.5-9.0 by adding DIEA and stirred overnight at room temperature. The crude product was separated and purified by YMC-Pack ODS-A semi-preparative HPLC.

The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-COOH confirmed by MALDI-TOF-MS with m/z=568.60 ([M+H]$^+$).

Preparation of HYNIC-PEG$_4$-OSu: HYNIC-PEG$_4$-COOH was dissolved in DMF, and NHS and EDC. HCl were added. The system was stirred at room temperature for 7 h. A 50% (v/v) aqueous ACN solution was added and the reaction solution was filtered, and the filtrate was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min.

Fractions of the objective product were collected, combined and lyophilized to give an expected product HYNIC-PEG$_4$-OSu confirmed by MALDI-TOF-MS with m/z=665.67 ([M+H]$^+$). Preparation of (AOC-rk-Dde)$_2$-Glu: AOC-rk-Dde and OSu$_2$-Glu-Boc were dissolved in DMF. The system was adjusted to pH 8.5-9.0 by adding DIEA, and stirred overnight at room temperature. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product (Aoc-rk-Dde)$_2$-Glu-Boc confirmed by MALDI-TOF-MS with m/z=3050.70 ([M+H]$^+$); the lyophilized product (Aoc-rk-Dde)$_2$-Glu-Boc was dissolved in 1 mL of TFA and reacted at room temperature for 5 min. The reaction solution was purged with nitrogen to dryness to give an expected product (Aoc-rk-Dde)$_2$-Glu confirmed by MALDI-TOF-MS with m/z=2950.58 ([M+H]$^+$).

Preparation of HYNIC-PEG$_4$-(Aoc-rk)$_2$: (Aoc-rk-Dde)$_2$-Glu and HYNIC-PEG$_4$-OSu were dissolved in DMF. The system was adjusted to pH 8.5-9.0 by adding DIEA, and stirred overnight at room temperature. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-(Aoc-rk-Dde)$_2$ confirmed by MALDI-TOF-MS with m/z=3501.16 ([M+H]$^+$); HYNIC-PEG$_4$-(Aoc-rk-Dde)$_2$ was dissolved in a 2% (v/v) solution of hydrazine hydrate in DMF, and the system was reacted at room temperature for 30 min. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA).

The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-(Aoc-rk)$_2$ confirmed by MALDI-TOF-MS with m/z=3172.75 ([M+H]$^+$); the structural formula is shown in FIG. 1.

Figure 2:
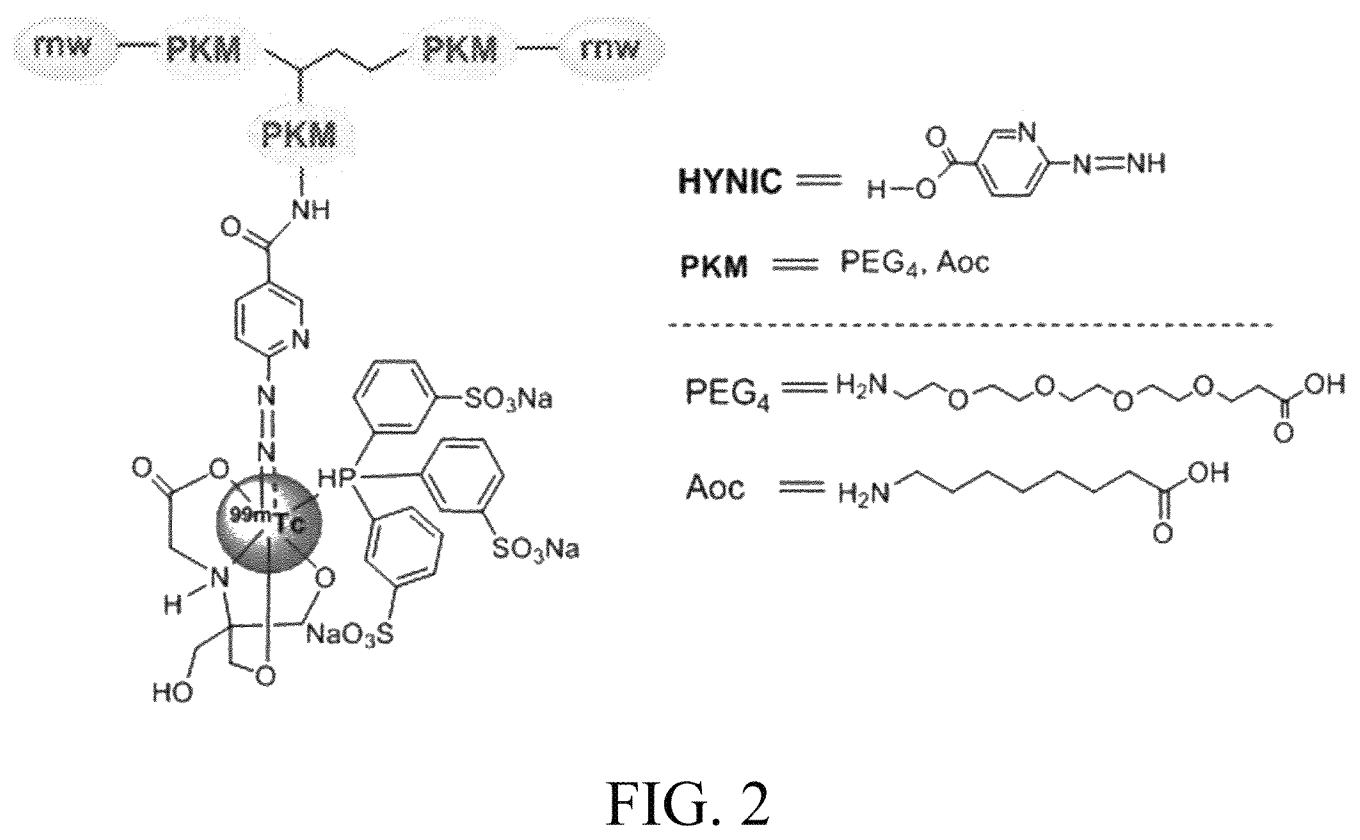

Preparation of $^{99m}$Tc-HYNIC-PEG$_4$-(Aoc-rk) 2:500 μL of a mixture containing 5.0 mg of trisodium triphenylphosphine-3,3',3"-trisulfonate (TPPTS), 6.5 mg of tricine, 38.5 mg of disodium succinate hexahydrate, 12.7 mg of succinic acid and 50 μg of HYNIC-PEG$_4$-(Aoc-rk)$_2$ was prepared in a 10 mL vial and lyophilized. 1.0-1.5 mL of Na$^{99m}$TcO$_4$ solution (10-35 mCi) was added to the lyophilized powder. The vial was incubated in a water bath at 100° C. for 20-25 min, and cooled at room temperature for 10 min after the reaction was completed to give the rk polypeptide radiopharmaceutical, the structural formula of which is shown in FIG. 2.

Figure 3:
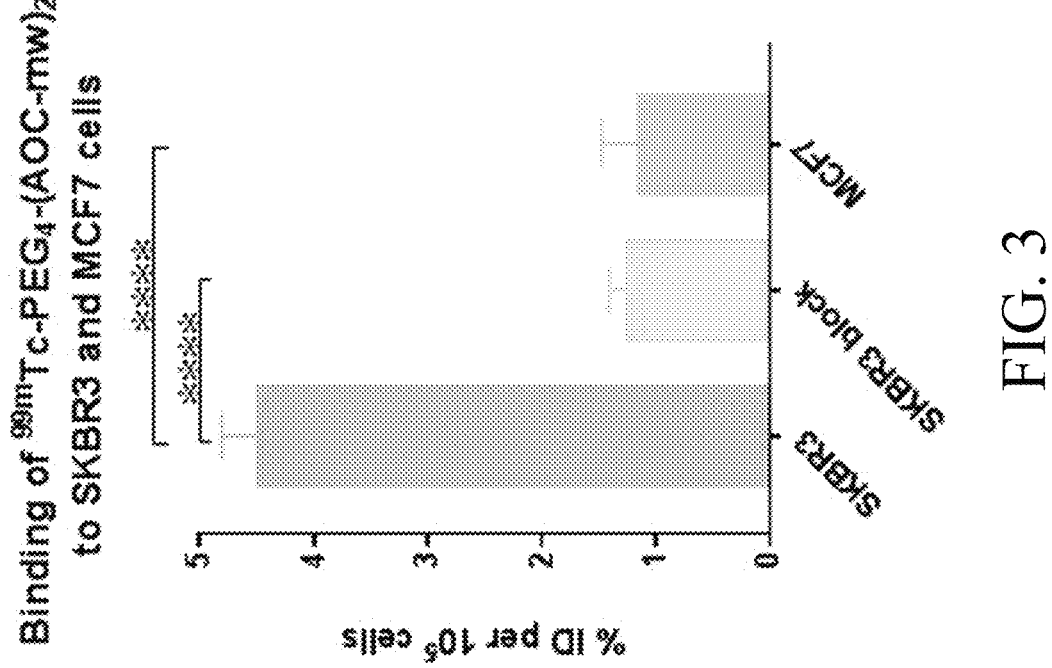
FIG. 3 illustrates a cell binding assay of $^{99m}$Tc-HYNIC-PEG$_4$-(Aoc-rk)$_2$, wherein rw denotes the rk polypeptide.

The rk polypeptide radiopharmaceuticals were sampled for radioactive HPLC analysis. The HPLC was conducted in an Agilent 1260 HPLC system equipped with a YMC-Pack ODS-A analytic column (250×4.6 mm, I.D. S-5 μm, 12 nm), and a 20-min gradient elution was performed at a flow rate of 1 mL/min, wherein the mobile A phase was deionized water (containing 0.05% TFA) and the mobile B phase was acetonitrile (containing 0.05% TFA). The elution gradients were 90% A and 10% B at beginning, and 30% A and 70% B at 20 min. The labeling rate of $^{99m}$Tc-HYNIC-PEG$_4$-(Aoc-rk)$_2$ was >95%, and the radiochemical purity was >98% as measured by HPLC with a Sep-Pak C$_{18}$ column. The results of a binding affinity assay of HYNIC-PEG$_4$-(Aoc-rk)$_2$ to HER2 are shown in FIG. 3: Human breast cancer cells SKBR3 of high HER2 expression and MCF7 of no HER2 expression were used as experimental samples, and $^{99m}$Tc-HYNIC-PEG$_4$-(Aoc-rk)$_2$ was used as a radioactive ligand specifically binding to HER2 receptor. In this cell binding assay, the binding capacities of $^{99m}$Tc-HYNIC-PEG$_4$-(Aoc-rk)$_2$ to SKBR3 and MCF7 were measured, with a blocking group treated with excessive HYNIC-PEG$_4$-(Aoc-rk)$_2$ to verify the binding specificity of $^{99m}$Tc-HYNIC-PEG$_4$-(Aoc-rk)$_2$ to SKBR3. The experimental result demonstrates binding rates of 4.49%, 1.14% and 1.24% per $10^5$ cells for $^{99m}$Tc-HYNIC-PEG$_4$-(Aoc-rk)$_2$ in SKBR3, MCF7 and SKBR3 blocking groups, respectively, with significant statistical differences, indicating that HYNIC-PEG$_4$-(Aoc-rk)$_2$ has higher and specific affinity to HER2.

Figure 4:
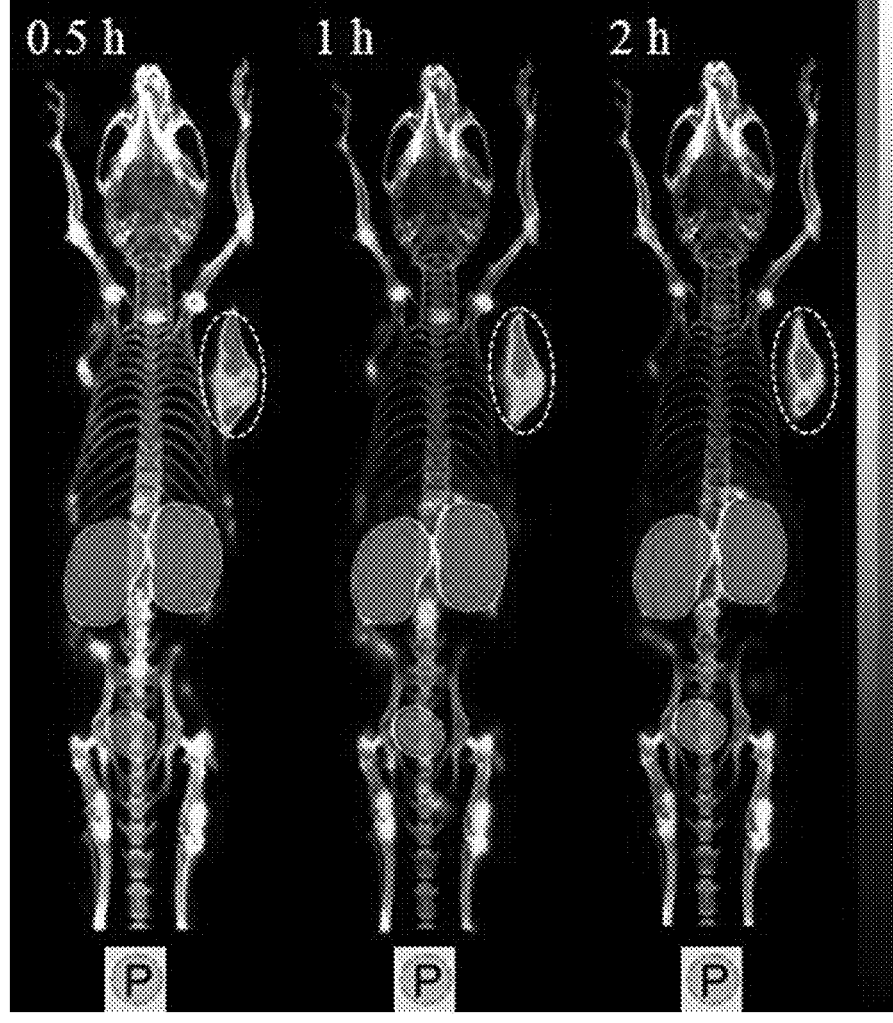
FIG. 4 illustrates SPECT/CT images in a NOD SCID murine SKBR3 breast tumor model at 0.5 h, 1 h and 2 h after injection of $^{99m}$Tc-HYNIC-PEG$_4$-(Aoc-rk)$_2$.
Figure 5:
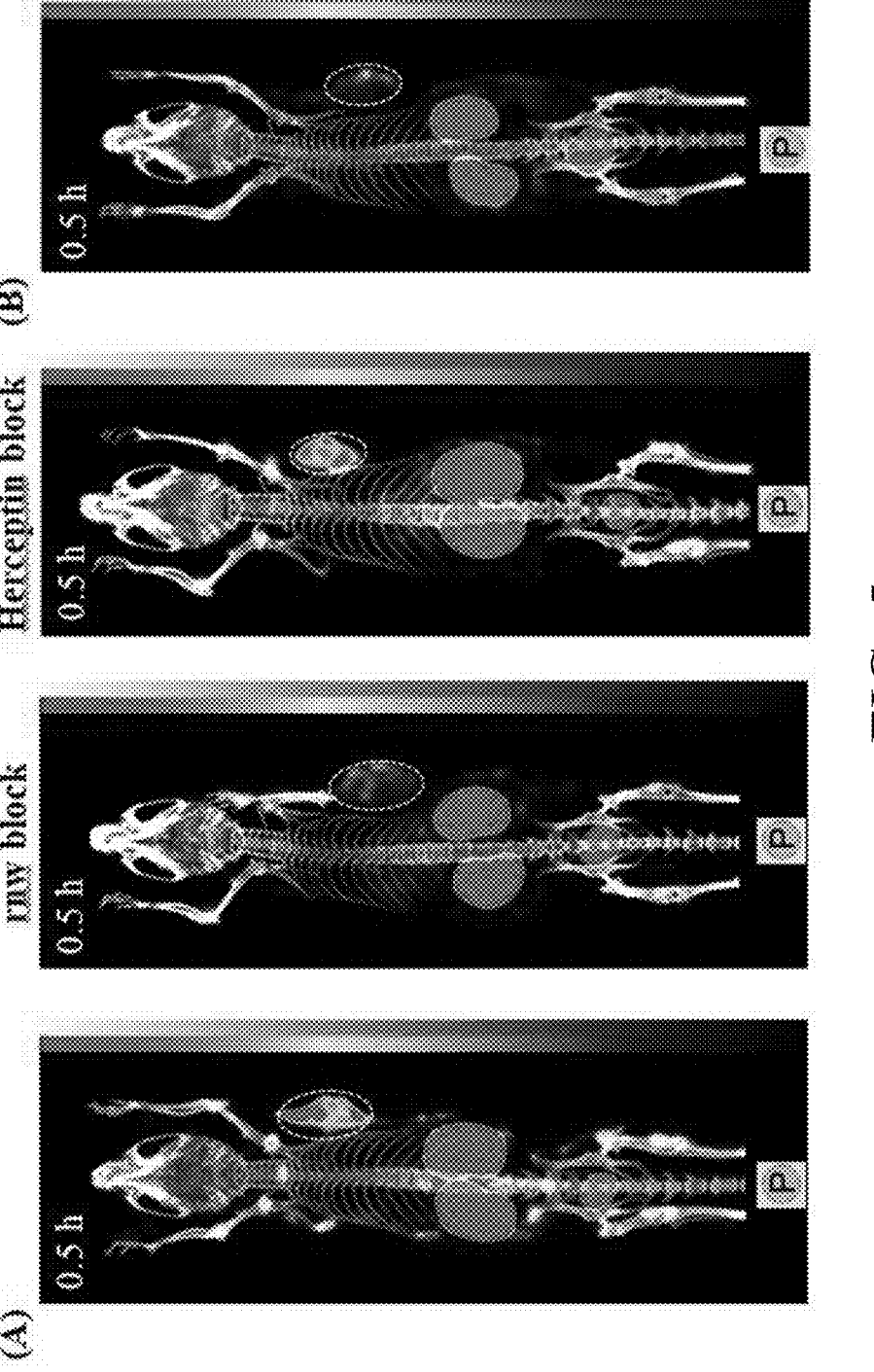
FIG. 5 illustrates (A) SPECT/CT images of experimental group, cold peptide blocking group and antibody blocking group in an SKBR3 breast tumor model at 0.5 h after injection of $^{99m}$Tc-HYNIC-PEG$_4$-(Aoc-rk)$_2$; and (B) an SPECT/CT image of $^{99m}$Tc-HYNIC-PEG$_4$-rk at 0.5 h in SKBR3 tumor model, wherein rnw denotes the rk polypeptide.
Figure 6:
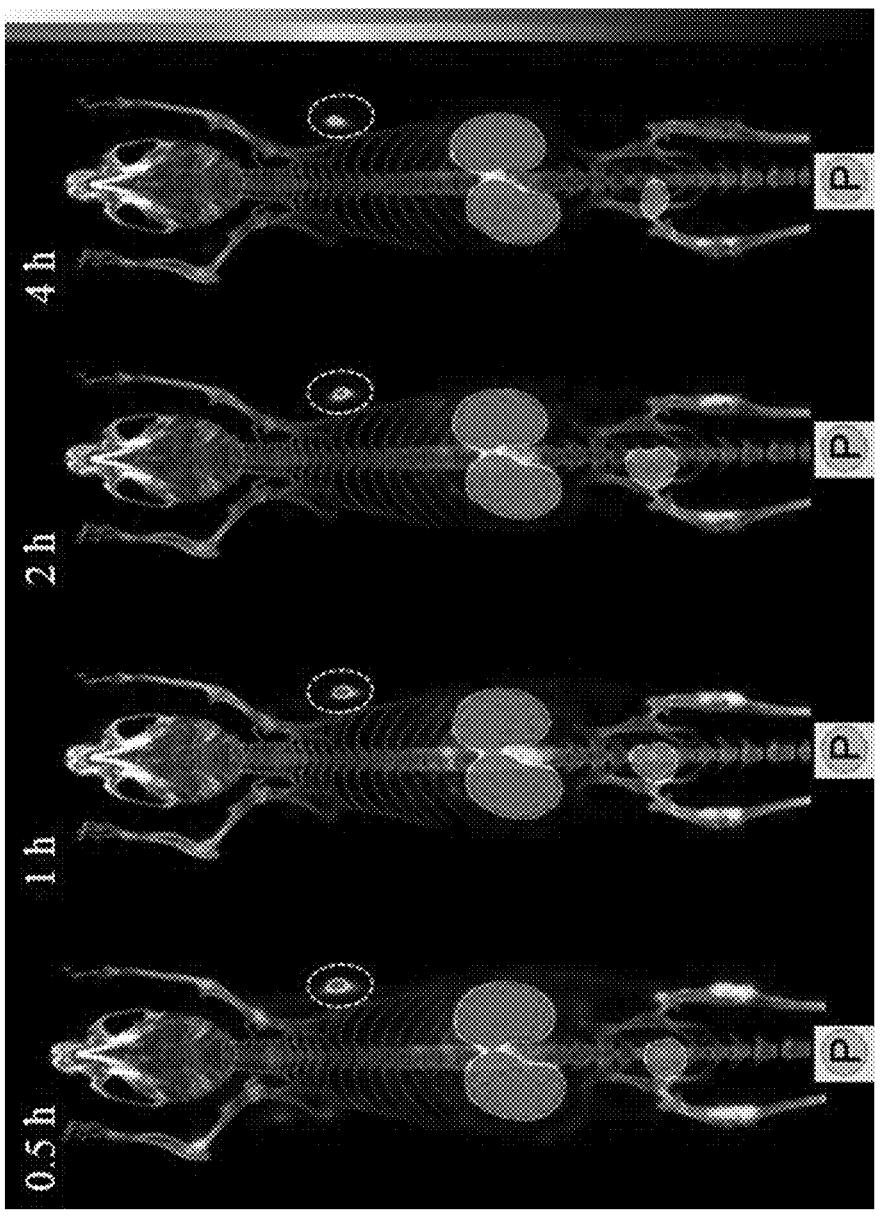
FIG. 6 illustrates delayed images of $^{99m}$Tc-HYNIC-PEG$_4$-(Aoc-rk)$_2$ in an NOD SCID mouse bearing early-stage SKBR3 breast tumor (V=30 mm$^3$).
Figure 7:
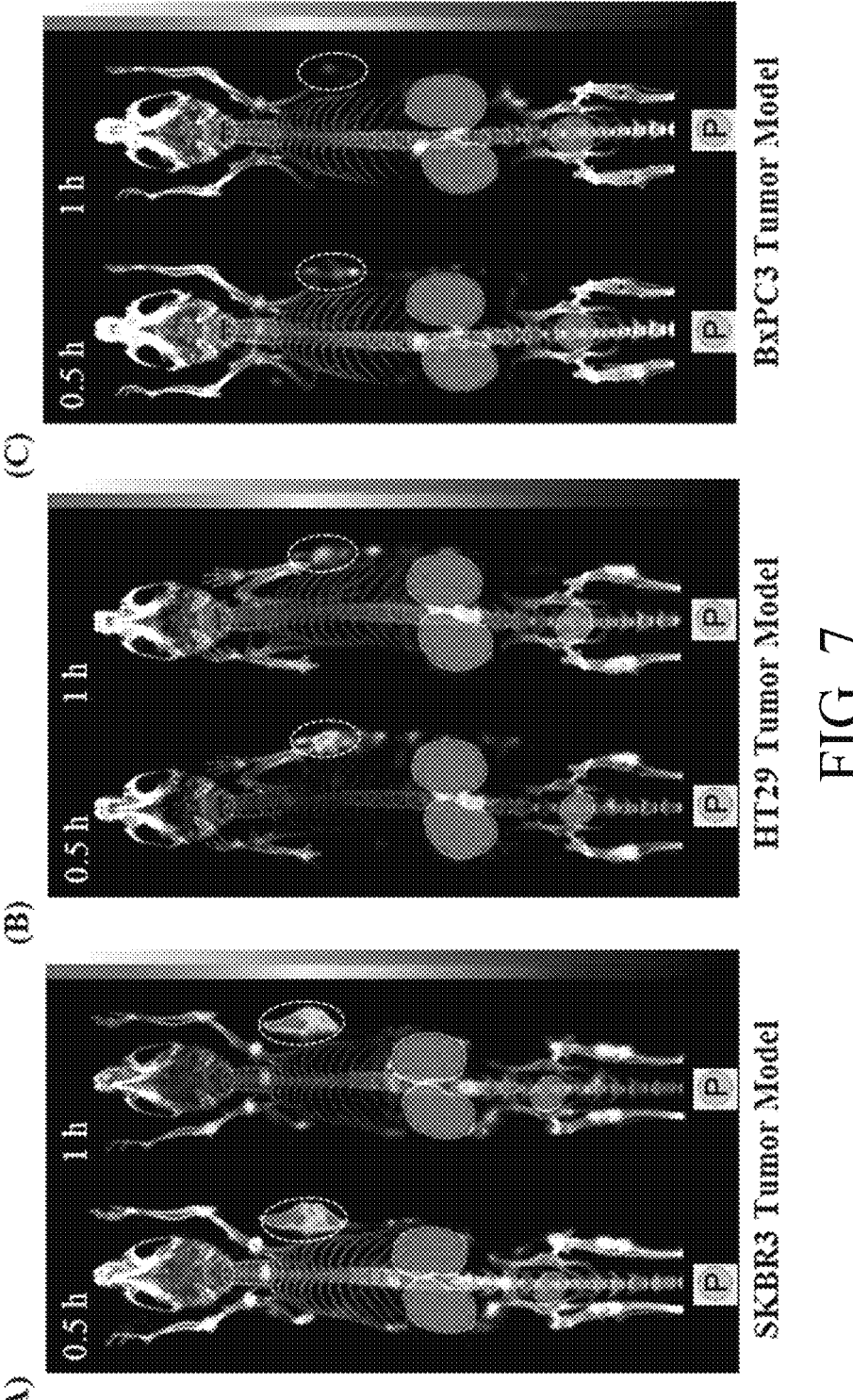
FIG. 7 illustrates SPECT/CT images of $^{99m}$Tc-HYNIC-PEG$_4$-(Aoc-rk)$_2$ in (A) an SKBR3 tumor model (high HER2 expression), (B) an HT29 tumor model (moderate HER2 expression), and (C) a BxPC3 tumor model (low HER2 expression).

SPECT/CT images of $^{99m}$Tc-HYNIC-PEG$_4$-(Aoc-rk)$_2$ in tumor-bearing mice are shown in FIG. 4: In an SKBR3 breast cancer model, the uptake of $^{99m}$Tc-HYNIC-PEG$_4$-(Aoc-rk)$_2$ in tumor was clearly visible and significantly higher than that of the monomer, and a clean whole-body background was observed, indicating suitability for early tumor diagnosis. The polypeptide demonstrated a prolonged retention time in tumor lesions, and tumor was still clearly visualized at 4 hours after injection. Thus the polypeptide is suitable for delayed imaging and more beneficial for tumor diagnosis. The imaging result is shown in FIG. 6. The result of the blocking group is shown in FIG. 5, demonstrating a significantly reduced uptake in tumor and suggesting a specific binding between the polypeptide and HER2. In Herceptin blocking group of SKBR3 breast cancer model, the uptake in tumor was substantially unchanged, indicating that the probe binds to a different site from the polypeptide, and can be used for monitoring the real-time efficacy in patients receiving Herceptin treatment. SPECT/CT images of $^{99m}$Tc-HYNIC-PEG$_4$-(Aoc-rk)$_2$ in a high HER2 expression tumor model (SKBR3 human breast cancer), a moderate HER2 expression tumor model (HT29 human colon cancer) and a low HER2 expression tumor model (BxPC3 human pancreas cancer) are shown in FIG. 7, and the result shows that the uptake of $^{99m}$Tc-HYNIC-PEG$_4$-(Aoc-rk)$_2$ is linearly related to the expression level of HER2, and can be used for detecting the expression of HER2 in tumor.

Figure 8:
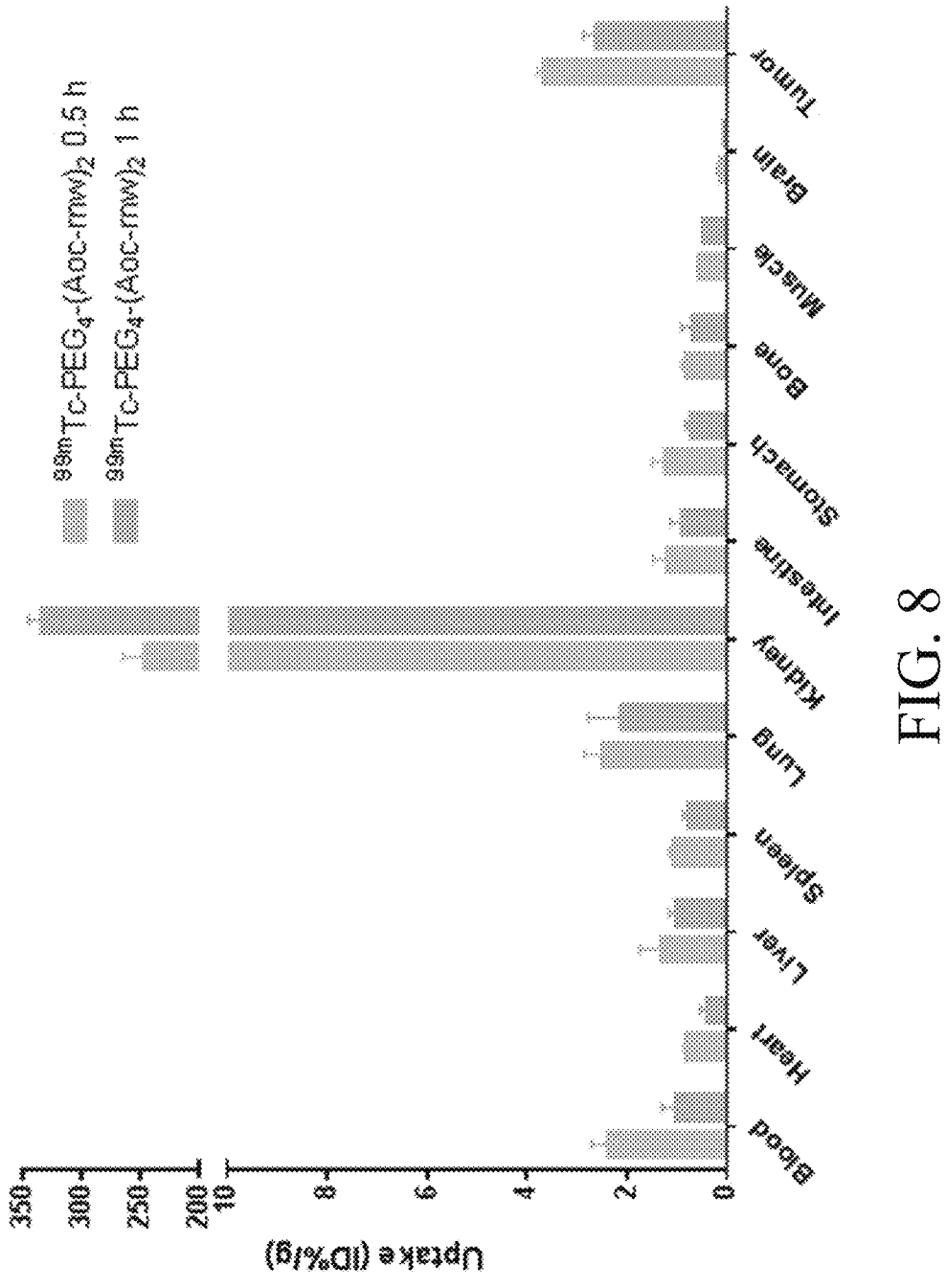
FIG. 8 illustrates in vivo biodistribution of $^{99m}$Tc-HYNIC-PEG$_4$-(Aoc-rk)$_2$ in an SKBR3 breast tumor model at 0.5 h and 1 h after injection, wherein rnw denotes the rk polypeptide.

The biodistribution of $^{99m}$Tc-HYNIC-PEG$_4$-(Aoc-rk)$_2$ in tumor-bearing mice: NOD SCID mice bearing SKBR3 tumor were randomized with 4 mice in each group. Each group of mice were injected with different $^{99m}$Tc-labeled polypeptides via tail vein, and sacrificed at 30 and 60 min after injection. Samples of blood and major organs were collected, weighed and measured for radiological counting, and the decay-corrected percent injection dose rate per gram of tissue (% ID/g) was calculated. The results of the experiment are shown in FIG. 8, in which the uptake in tumor at 30 min was 3.7% ID/g, and the uptake was low in blood and organs other than kidney.

Correlation between uptake of $^{99m}$Tc-HYNIC-PEG$_4$-(Aoc-rk)$_2$ in tumor and HER2 expression level: tumor cells with different HER2 expression levels, including human breast cancer cell lines SKBR3, MCF7 and MDA-MB-468, human colorectal cancer cell line HT29 and human pancreatic cancer cell line BxPC3, were selected and subjected to flow cytometry for quantitative analysis of HER2 expression in cells. Then the tumor models of the cells were subjected to SPECT/CT imaging, and the uptake in tumor was quantitatively analyzed. Finally, the correlation between HER2 expression and the uptake in tumor was investigated.

Flow cytometry: The cells were digested using 0.25% EDTA/pancreatin, blocked for 15 min, centrifuged, washed with PBS, and divided into a treatment group and a control group. A PE directly labeled anti-human HER2 antibody (1:100 dilution) was added to the treatment group, and the control group was resuspended with the same volume of PBS. The two groups were incubated for 0.5 h in the dark at 4° C., washed for 3 times using cold PBS, and analyzed on a flow cytometer. The mean fluorescence intensity (MFI) of the bound antibody on each cell was calculated through a standard flow cytometry curve.

SPECT/CT imaging: Different tumor models with similar tumor sizes were selected, administered with 1 mCi $^{99m}$Tc-HYNIC-PEG$_4$-(Aoc-rk)$_2$ through tail vein, and subjected to SPECT/CT imaging 0.5 h later. The SPECT images were reconstructed after imaging, fused with the CT image to give 3D images of the mouse, and the tumor lesion was extracted by In VivoScope software for quantitative analysis.

Analysis of correlation between HER2 expression level and uptake in tumor: the linear relationship between HER2 expression level (MFI) and uptake in tumor (% ID/g) was plotted using prism 7.0 software, and the $R^2$ value was calculated.

Figure 14:
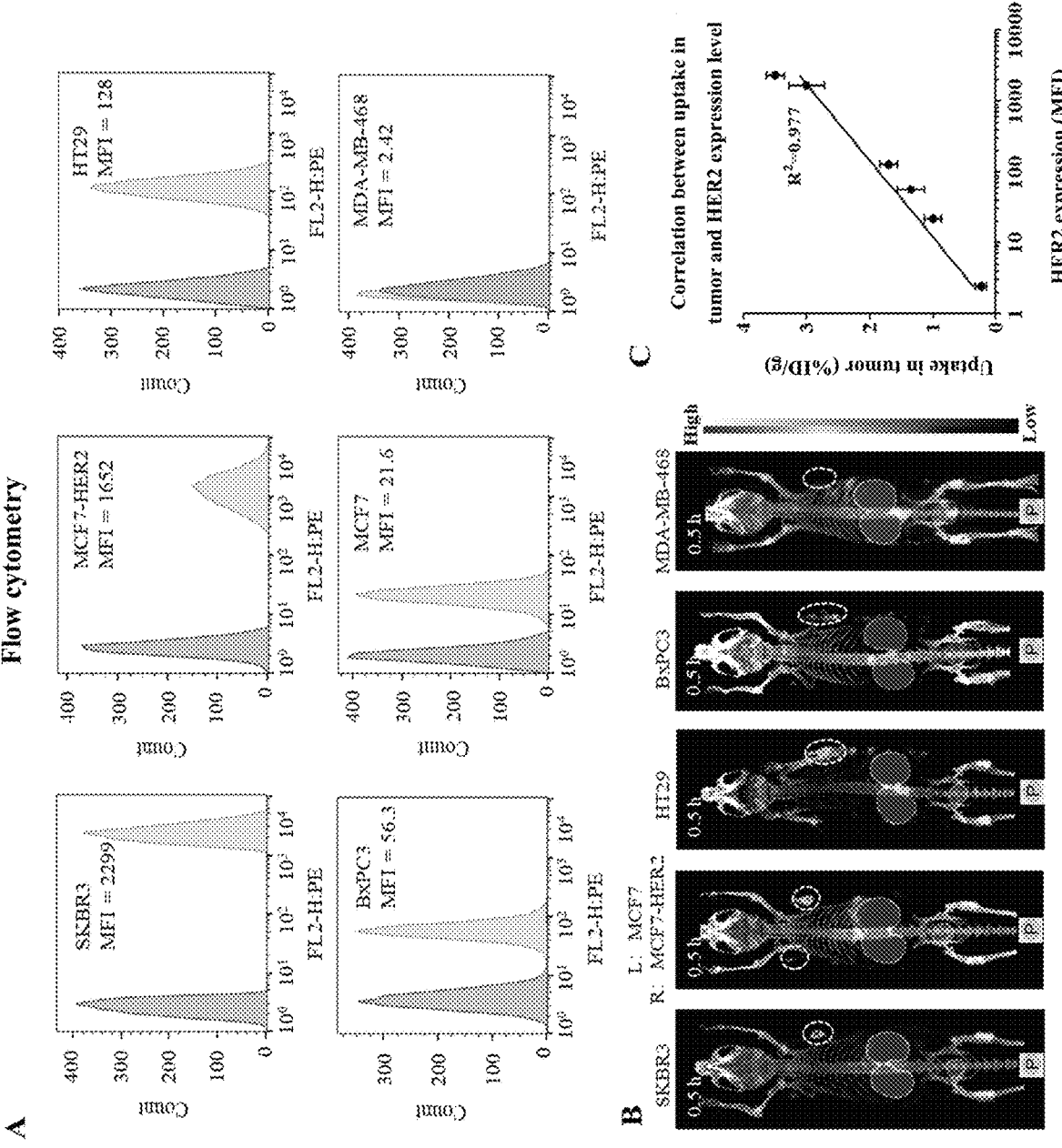
FIG. 14 illustrates (a) flow cytometric patterns; (B) representative SPECT/CT images; and (C) a correlation between an HER2 expression level and tumor uptake.

The experimental result is shown in FIG. 14, the uptake in tumor and the HER2 expression level are in positive correlation ($R^2$=0.977), indicating that the uptake of the probe $^{99m}$Tc-HYNIC-PEG$_4$-(Aoc-rk)$_2$ in tumor can accurately reflect the expression level of HER2.

Figure 15:
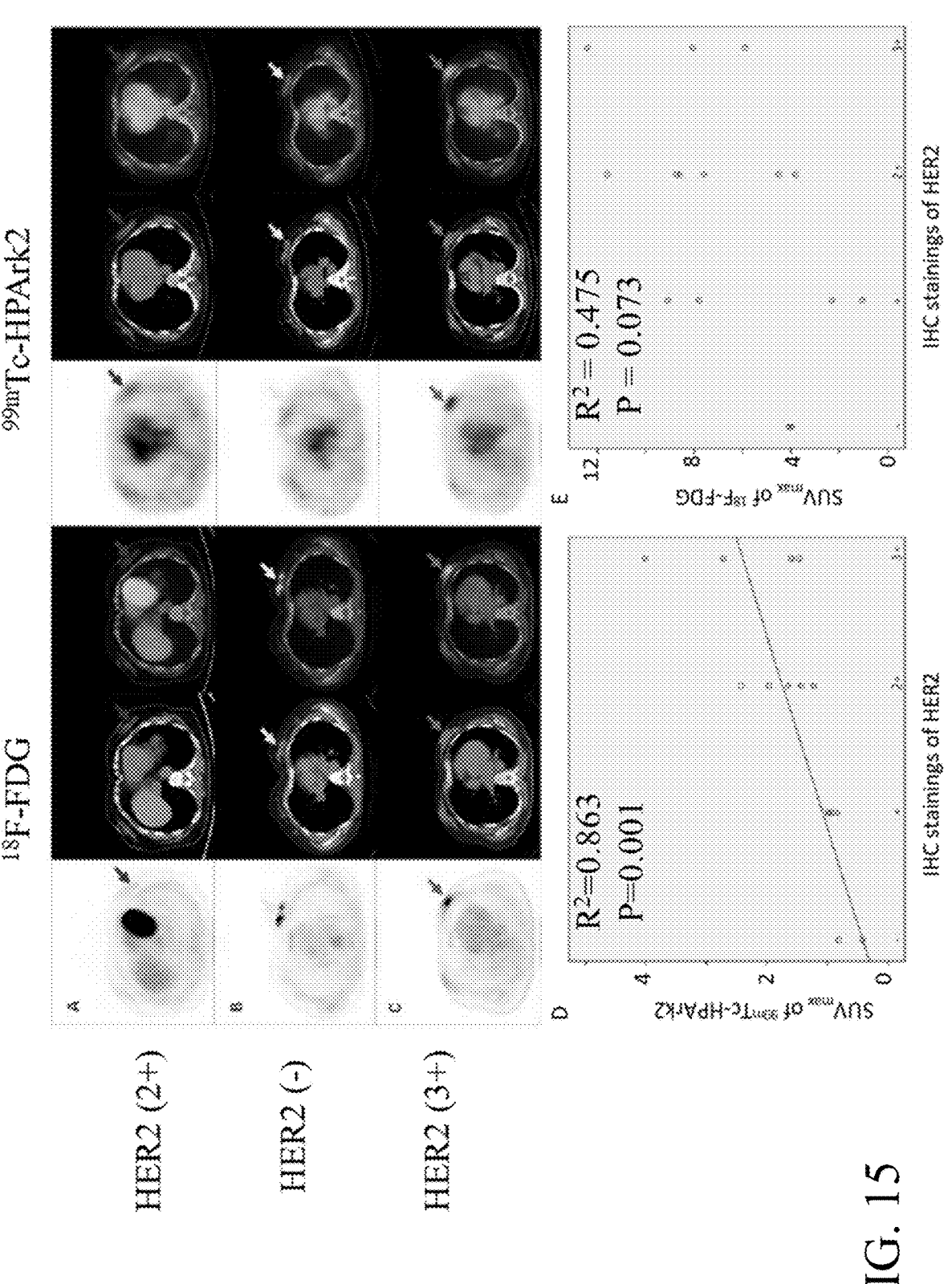
FIG. 15 illustrates 18F-FDG PET/CT images (left) and $^{99m}$Tc-HPArk2 SPECT/CT images (right) in patients with pathologically confirmed (A) HER2 (2+), (B) HER2 (−) and (C) HER2 (3+) breast tumors; (D) a correlation between SUV$_{max}$ of $^{99m}$Tc-HPArk2 SPECT/CT and HER2 expression level (R$^2$=0.863, P=0.001); and (E) a correlation between SUV$_{max}$ of $^{18}$F-FDG PET/CT and HER2 expression level (R$^2$=0.475, P=0.073).

SPECT/CT imaging of $^{99m}$Tc-HYNIC-PEG$_4$-(Aoc-rk)$_2$ in breast cancer patients: with approval by the Ethics Review Committee of the Peking Union Medical College Hospital and informed consent, 20 female patients with suspected breast cancer by molybdenum target X-ray or ultrasonography were recruited and subjected to SPECT/CT imaging and PET/CT imaging 1 week before surgery. The patients were administered intravenously with 11.1 MBq (0.3 mCi)/kg body weight of $^{99m}$Tc-HYNIC-PEG$_4$-(Aoc-rk)$_2$ 30 min before SPECT/CT scan, and 5.6 MBq (0.15 mCi)/kg body weight of $^{18}$F-FDG 60 min before PET/CT scan. 15 of these patients were pathologically diagnosed with breast cancer, among which 6 demonstrated ipsilateral lymph node metastasis. The results of this clinical trial are shown in FIG. 15. In the 15 patients, the tumor was more accurately imaged by $^{99m}$Tc-HYNIC-PEG$_4$-(Aoc-rk)$_2$ in 14 patients (93%); in the 6 patients with lymph node metastasis, 5 patients showed metastasis (83%), and in last one patient only slight lymph node metastasis was observed. The uptake intensity (SUV$_{max}$) of $^{99m}$Tc-HYNIC-PEG$_4$-(Aoc-rk)$_2$ in breast cancer was significantly correlated with immunohistochemical results for HER2 ($R^2$=0.863, P=0.001). No adverse effect related to the radiopharmaceutical was found during the clinical trial.

Example 2

This example exemplifies $^{99m}$Tc-HYNIC-PEG$_4$-(PEG$_4$-rk)$_2$ as the polypeptide radiopharmaceutical and the method for preparing the same.

In $^{99m}$Tc-HYNIC-PEG$_4$-(PEG$_4$-rk)$_2$, the rk polypeptide monomer is linear polypeptide rnwelrlk of D-amino acids, the rk polypeptide dimer is formed by conjugating the linker PEG$_4$ with the rk polypeptide monomer and then dimerizing two rk polypeptide monomers conjugated with PEG$_4$, a radionuclide $^{99m}$Tc labels the rk polypeptide dimer through the bifunctional chelating agent HYNIC, and a pharmacokinetic modifying molecule PEG$_4$ is conjugated between the rk polypeptide dimer and the bifunctional chelating agent. The rk polypeptide radiopharmaceutical is $^{99m}$Tc-HYNIC-PEG$_4$-(PEG$_4$-rk)$_2$. The rk polypeptide radiopharmaceutical is a colorless transparent liquid injection.

The method for preparing $^{99m}$Tc-HYNIC-PEG$_4$-(PEG$_4$-rk)$_2$ comprises the following steps:

Preparation of HYNIC-PEG$_4$-COOH: Fmoc-protected PEG$_4$-COOH was dissolved in DMF, and piperidine was added to make a final concentration of 20%. The system was reacted at room temperature for 20 min, and 10 mL of diethyl ether was added at 4° C. to precipitate PEG$_4$-COOH. The mixture was centrifuged at 4000 rpm at 4° C. for 5 min and the supernatant was discarded. The precipitate was washed with diethyl ether at 4° C. for 3 times, and residual diethyl ether was removed by rotary evaporation to give NH$_2$-PEG$_4$-COOH. HYNIC-NHS and NH$_2$-PEG$_4$-COOH were dissolved in DMF. The system was adjusted to pH 8.5-9.0 by adding DIEA and stirred overnight at room temperature. The crude product was separated and purified by YMC-Pack ODS-A semi-preparative HPLC.

The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-COOH confirmed by MALDI-TOF-MS with m/z=568.60 ([M+H]$^+$).

Preparation of HYNIC-PEG$_4$-OSu: HYNIC-PEG$_4$-COOH was dissolved in DMF, and NHS and EDC·HCl were added. The system was stirred at room temperature for 7 h before a 50% (v/v) aqueous ACN solution was added. The reaction solution was filtered, and the filtrate was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-OSu confirmed by MALDI-TOF-MS with m/z=665.67 ([M+H]$^+$).

Preparation of (PEG$_4$-rk-Dde)$_2$-Glu: PEG$_4$-rk-Dde and OSu$_2$-Glu-Boc were dissolved in DMF. The system was adjusted to pH 8.5-9.0 by adding DIEA, and stirred overnight at room temperature. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product (PEG$_4$-rk-Dde)$_2$-Glu-Boc confirmed by MALDI-TOF-MS with m/z=3262.85 ([M+H]$^+$); the lyophilized product (PEG$_4$-rk-Dde)$_2$-Glu-Boc was dissolved in 1 mL of TFA and reacted at room temperature for 5 min. The reaction solution was purged with nitrogen to dryness to give an expected product (PEG$_4$-rk-Dde)$_2$-Glu confirmed by MALDI-TOF-MS with m/z=3162.73 ([M+H]$^+$).

Preparation of HYNIC-PEG$_4$-(PEG$_4$-rk)$_2$: (PEG$_4$-rk-Dde)$_2$-Glu and HYNIC-PEG$_4$-OSu were dissolved in DMF. The system was adjusted to pH 8.5-9.0 by adding DIEA, and stirred overnight at room temperature. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-(PEG$_4$-rk-Dde)$_2$ confirmed by MALDI-TOF-MS with m/z=3713.32 ([M+H]$^+$); HYNIC-PEG$_4$-(PEG$_4$-rk-Dde)$_2$ was dissolved in a 2% (v/v) solution of hydrazine hydrate in DMF, and the system was reacted at room temperature for 30 min. The crude product was separated and purified by YMC-Pack ODS-A semi-preparative HPLC. The HPLC was conducted in an Agilent 1260 HPLC system equipped with a YMC-Pack ODS-A semi-preparative column (250×10 mm, I.D. S-5 μm, 12 nm), and a 30-min gradient elution was performed at a flow rate of 4 mL/min, wherein the mobile A phase was deionized water (containing 0.05% TFA) and the mobile B phase was acetonitrile (containing 0.05% TFA). The elution gradients were 90% A and 10% B at beginning, 50% A and 50% B at 25 min, and 90% A and 10% B at 30 min. Fractions of the objective product were collected, combined and lyophilized to give an expected product HYNIC-PEG$_4$-(PEG$_4$-rk)$_2$ confirmed by MALDI-TOF-MS with m/z=3384.91 ([M+H]$^+$).

Figure 9:
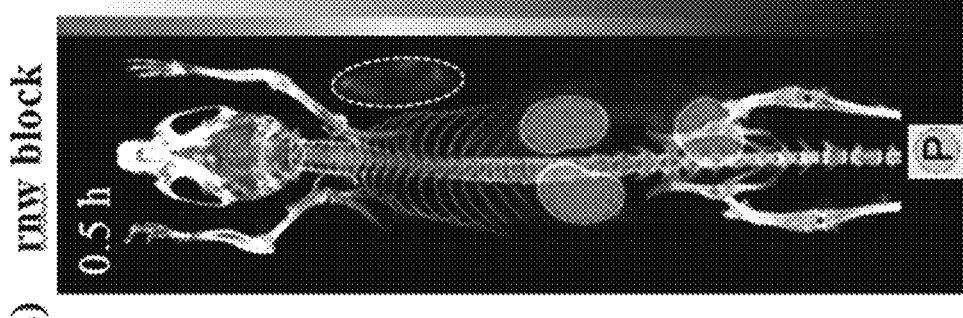
FIG. 9 illustrates (A) SPECT/CT images in an SKBR3 breast tumor model at 0.5 h, 1 h and 2 h; and (B) an SPECT/CT image in a cold peptide blocking group at 0.5 h after injection of $^{99m}$Tc-HYNIC-PEG$_4$-(PEG$_4$-rk)$_2$, wherein rnw denotes the rk polypeptide.
Figure 9:
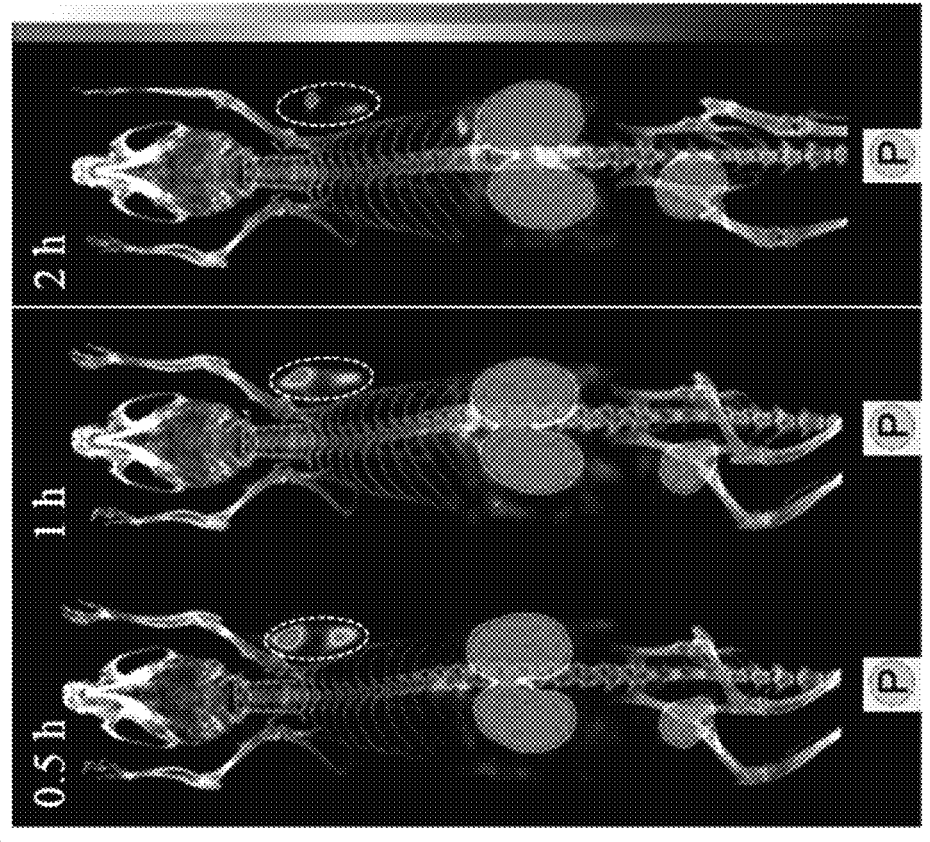

Preparation of $^{99m}$Tc-HYNIC-PEG$_4$-(PEG$_4$-rk) 2:500 μL of a mixture containing 5.0 mg of trisodium triphenylphosphine-3,3', 3"-trisulfonate (TPPTS), 6.5 mg of tricine, 38.5 mg of disodium succinate hexahydrate, 12.7 mg of succinic acid and 50 μg of HYNIC-PEG$_4$-(PEG$_4$-rk)$_2$ was prepared in a 10 mL vial and lyophilized. 1.0-1.5 mL of Na$^{99m}$TcO$_4$ solution (10-35 mCi) was added to the lyophilized powder. The vial was incubated in a water bath at 100° C. for 20-25 min, and cooled at room temperature for 10 min after the reaction is completed to give the rk polypeptide radiopharmaceutical. The rk polypeptide radiopharmaceuticals were sampled for radioactive HPLC analysis. The HPLC was conducted in an Agilent 1260 HPLC system equipped with a YMC-Pack ODS-A analytic column (250× 4.6 mm, I.D. S-5 μm, 12 nm), and a 20-min gradient elution was performed at a flow rate of 1 mL/min, wherein the mobile A phase was deionized water (containing 0.05% TFA) and the mobile B phase was acetonitrile (containing 0.05% TFA). The elution gradients were 90% A and 10% B at beginning, and 30% A and 70% B at 20 min. The labeling rate of $^{99m}$Tc-HYNIC-PEG$_4$-(PEG$_4$-rk)$_2$ was >95%, and the radiochemical purity was >98% as measured by a Sep-Pak C$_{18}$ column. SPECT/CT images of $^{99m}$Tc-HYNIC-PEG$_4$-(PEG$_4$-rk)$_2$ in tumor-bearing mice are shown in FIG. 9: In an SKBR3 breast cancer model, the uptake of $^{99m}$Tc-HYNIC-PEG$_4$-(PEG$_4$-rk)$_2$ in tumor was clearly visible and significantly higher than that of the monomer, and a clean whole-body background was observed. The result of the blocking group demonstrates a significantly reduced tumor uptake, suggesting a specific binding between the polypeptide and HER2.

Comparative Example 1

Chinese Patent Publication No. CN 109045313A discloses a compound $^{99m}$Tc-HYNIC-PKM-ref (PKM=PEG$_n$, n=1-24) based on a polypeptide sequence of refvffly (the linear polypeptide comprises a D-amino acid sequence of Arg-Glu-Phe-Val-Phe-Phe-Leu-Tyr, and is referred to as ref polypeptide for short herein), which is also a polypeptide radiopharmaceutical targeting HER2-positive tumor. On this basis, the present invention improved the compound.

Figure 10:
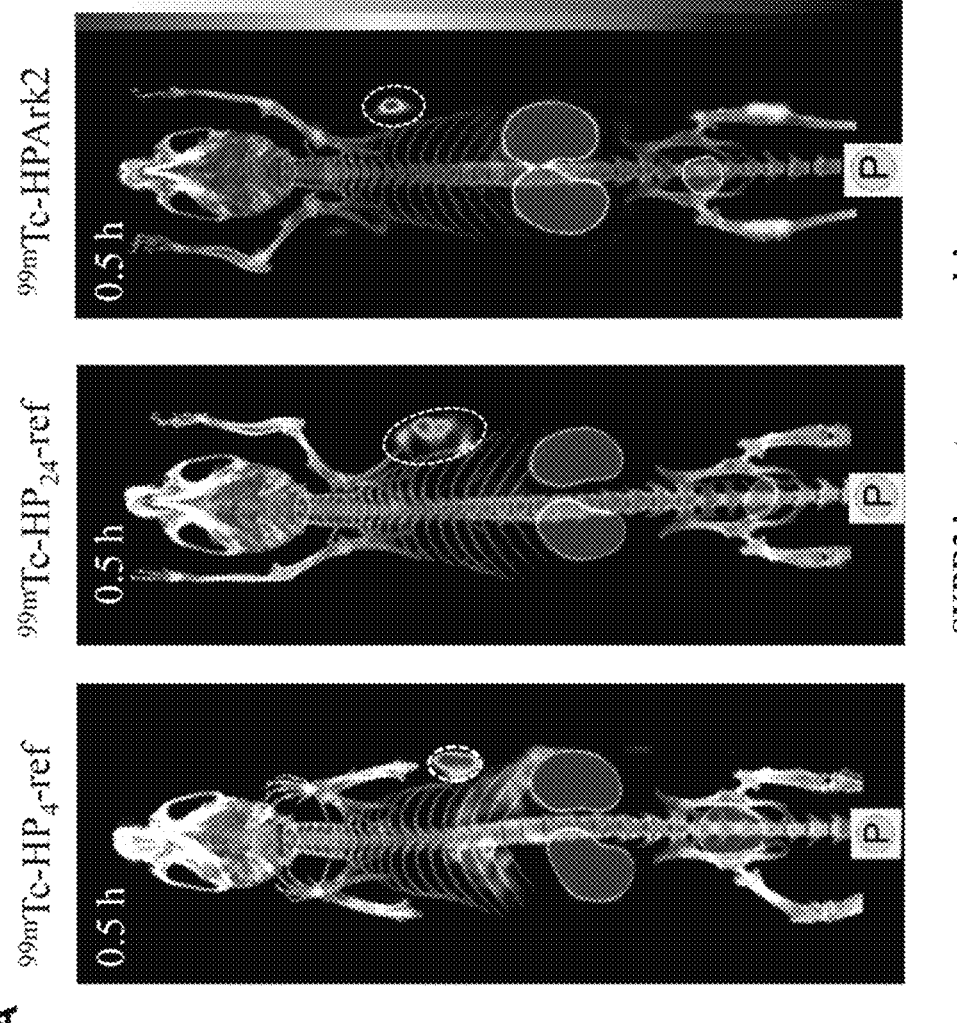
FIG. 10 illustrates the results of image comparison and quantitative data analysis of an HER2-positive model (an SKBR3 breast tumor model).
Figure 10:
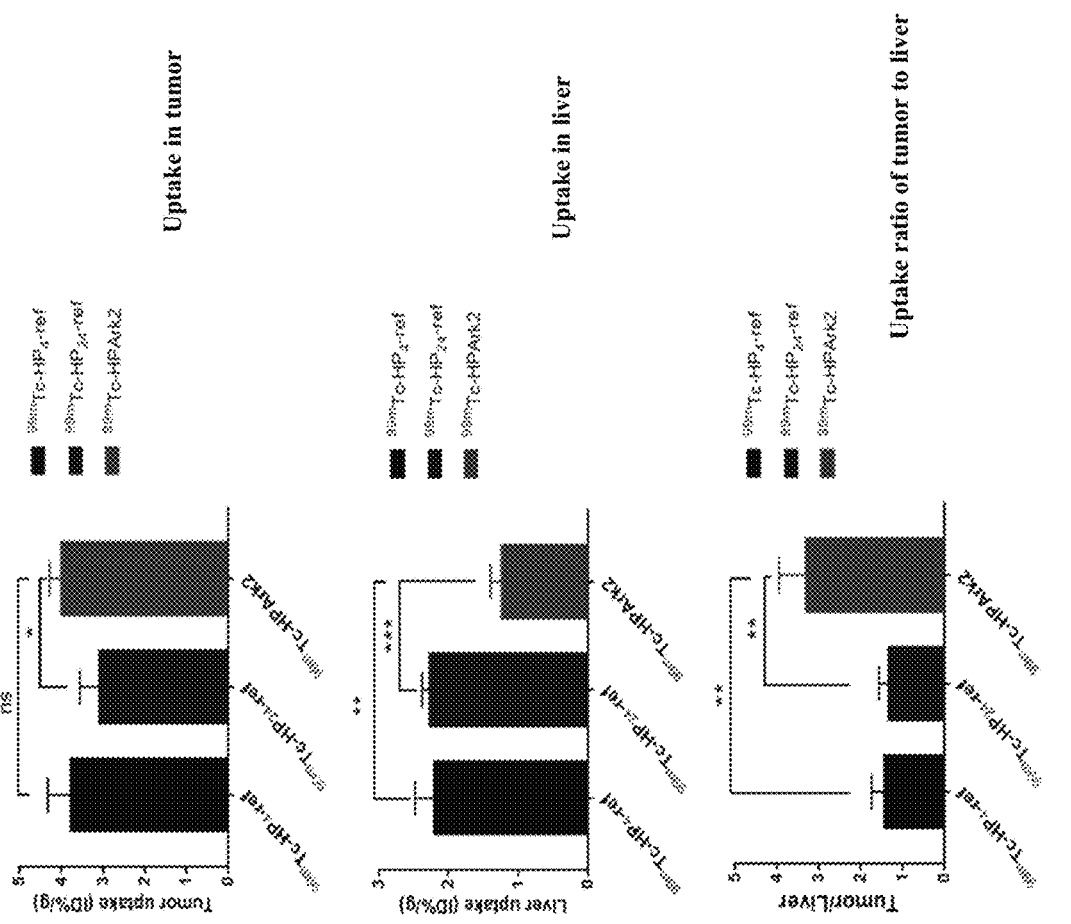
Figure 10:

The water solubility of the polypeptide selected herein is superior to that of refvffly polypeptide. The specificity of the improved compound is superior to that of $^{99m}$Tc-HYNIC-PKM-ref. See FIG. 10 for details. FIG. 10 panel A shows the results of imaging comparison and quantitative analysis of the same model. FIG. 10 panel B shows the result of the quantitative analysis in FIG. 10 panel A.

As shown in FIG. 10, the contrast agent $^{99m}$Tc-HYNIC-PEG$_4$-(Aoc-rk)$_2$ (abbreviated $^{99m}$Tc-HPArk2 in the figure) of the present invention has a significant difference in the imaging effect in HER2-positive breast cancer model, as compared with the contrast agent $^{99m}$Tc-HYNIC-PEG$_4$-ref (abbreviated $^{99m}$Tc-HP$_4$-ref) or $^{99m}$Tc-HYNIC-PEG$_{24}$-ref (abbreviated $^{99m}$Tc-HP$_{24}$-ref) disclosed in Patent No. CN 109045313A. Since the present invention is ultimately intended for in situ imaging of breast cancer, the uptake in tumor and background uptake in liver in the thorax are most crucial. $^{99m}$Tc-HPArk2 demonstrated higher uptake in tumor than that of $^{99m}$Tc-HP$_{24}$-ref, with no significant difference from $^{99m}$Tc-HP$_4$-ref. Whereas hepatic uptake of $^{99m}$Tc- HPArk2 was lowest, as compared to 99 mm Tc-HP$_4$-ref and $^{99m}$Tc-HP$_{24}$-ref. Thus the uptake ratio of tumor to liver was highest for $^{99m}$Tc-HPArk2. This is especially critical for breast cancer tumors in situ in the thorax, since the contrast agent $^{99m}$Tc-HPArk2 of the present invention is more advantageous in imaging breast cancer lesions in situ.

Figure 11:
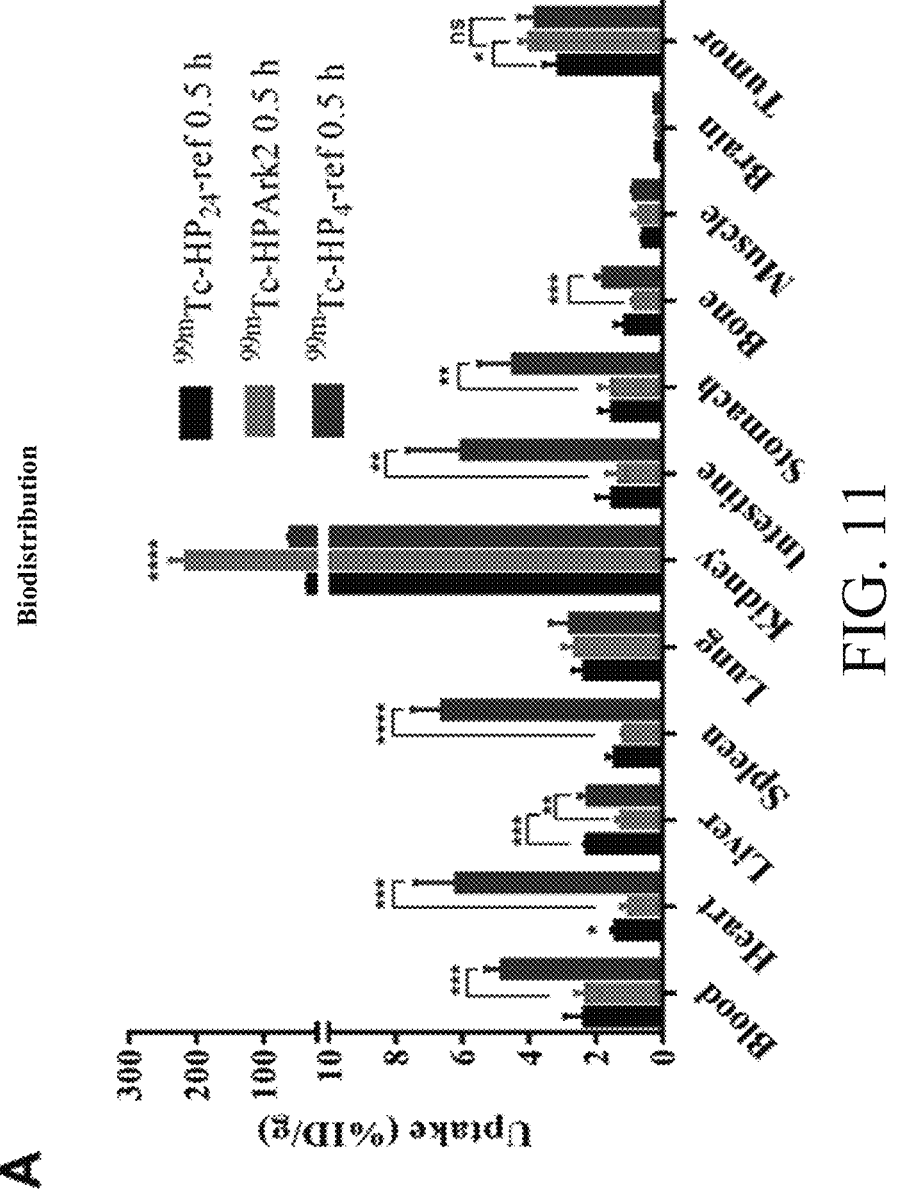
FIG. 11 illustrates biodistribution data and an uptake ratio of tumor to normal tissue in an HER2-positive tumor model.
Figure 11:
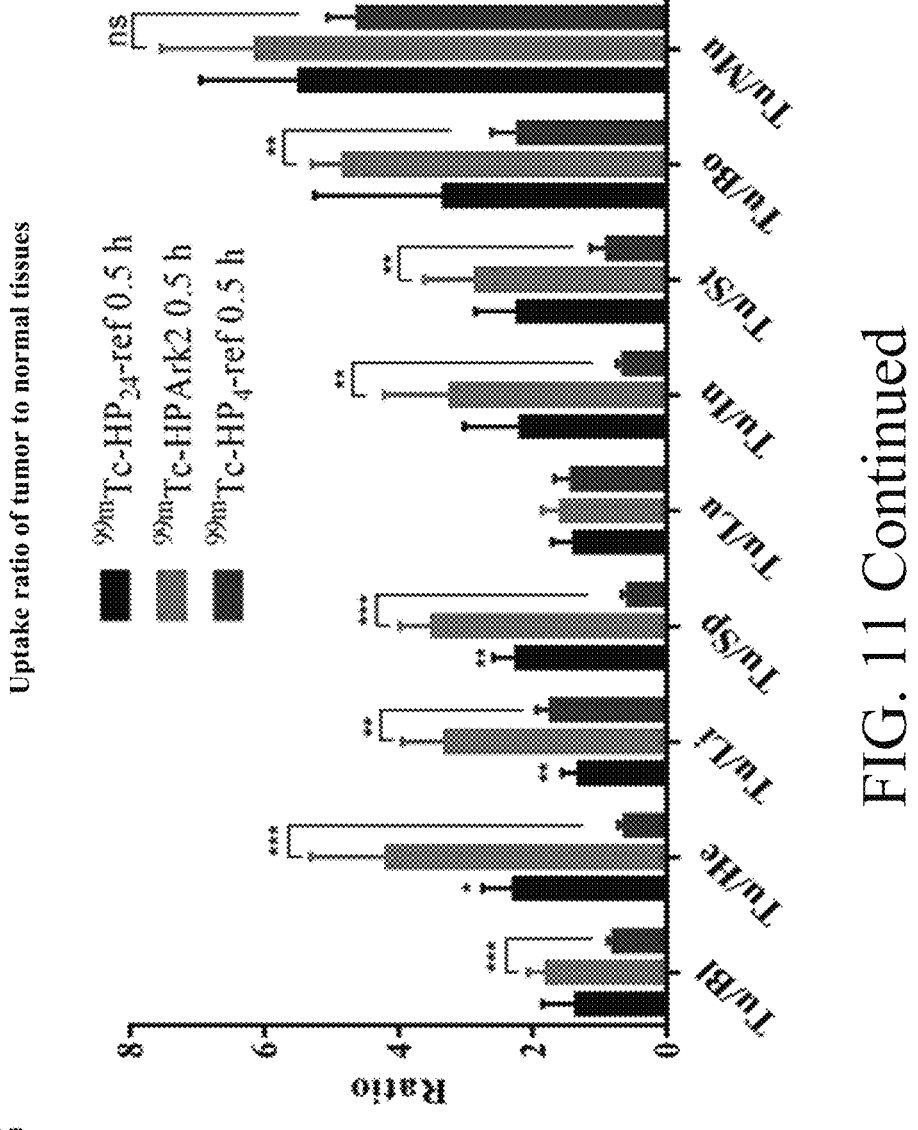

The specific difference of in vivo pharmacokinetics between the present invention and the radiopharmaceutical disclosed in Patent No. CN 109045313 A is shown in FIG. 11. FIG. 11 illustrates the uptake in tumor and comparison of data corresponding to the images in FIG. 10. FIG. 11 illustrates quantitative data, and FIG. 10 shows visual image data. FIG. 11 panel B illustrates the results of calculations from FIG. 11 panel A. The uptakes in tumor and the organs were compared and analyzed. As can be seen from FIG. 11, the radiopharmaceutical $^{99m}$Tc-HPArk2 of the present invention in tumor demonstrates a relatively higher uptake in tumor than those of $^{99m}$Tc-HP$_4$-ref and $^{99m}$Tc-HP$_{24}$-ref, which improves the sensitivity of tumor imaging and is capable of imaging smaller tumors. As is also seen in FIG. 10, a smaller tumor was visualized by $^{99m}$Tc-HPArk2 imaging, and the imaging effect is guaranteed. Uptake of $^{99m}$Tc-HPArk2 in blood, heart, liver, spleen, intestine, stomach, bone and other tissues was relatively lower, resulting in relatively higher ratios of tumor to normal tissues such as blood, heart, liver, spleen, intestine and stomach. Therefore, the contrast ratio for imaging is better, and particularly, the low uptake in heart and liver in the chest cavity may facilitate clear imaging of the in-situ tumor of the breast cancer.

Figure 12:
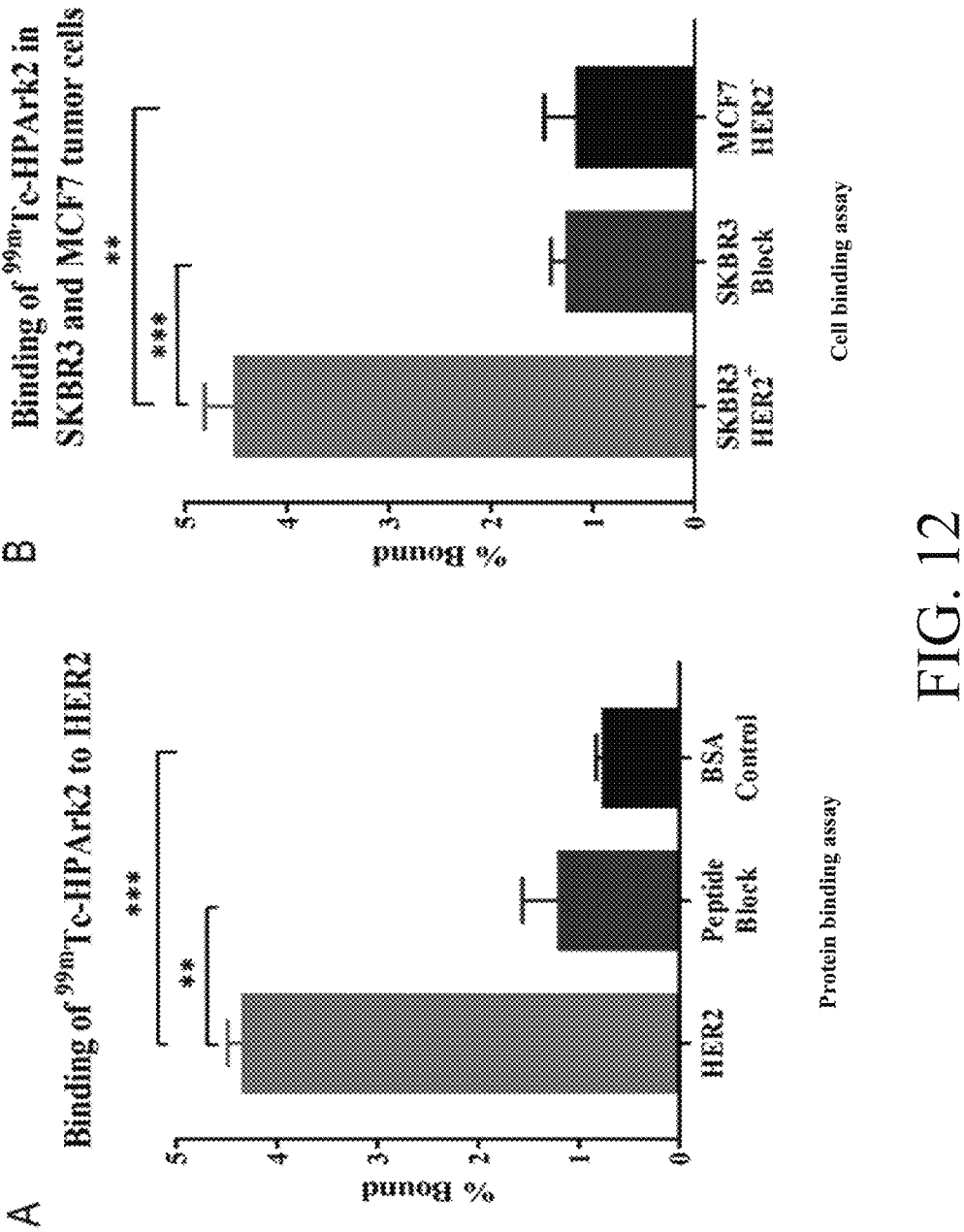
FIG. 12 illustrates results of detecting HER2 binding specificity of radiopharmaceutical $^{99m}$Tc-HPArk 2 to protein and cell.
Figure 13:
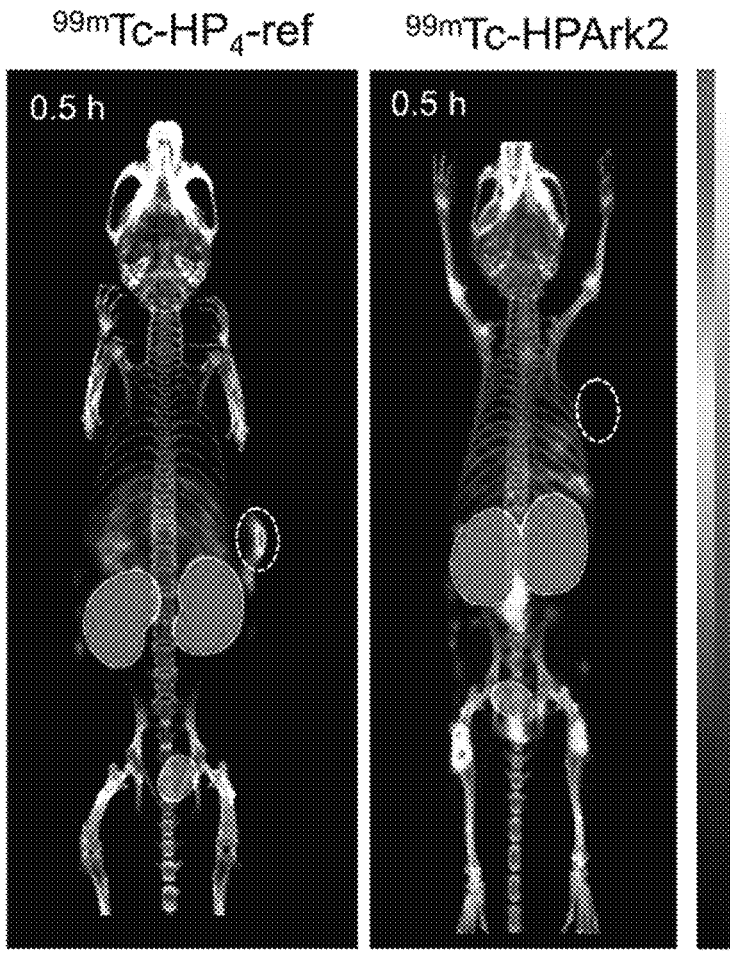
FIG. 13 illustrates images of $^{99m}$Tc-HYNIC-PEG$_4$-(Aoc-rk)$_2$ (abbreviated $^{99m}$Tc-HPArk2) and $^{99m}$Tc-HP$_4$-ref in an HER2-negative/EGFR-positive tumor model.

As shown in FIG. 12, in order to verify the effect of the pharmaceutical of the present invention, HER2 specificity detection of the radiopharmaceutical was performed. The radiopharmaceutical showed good specificity at both protein and cellular levels.

Since EGFR and HER2 are members of the same family and have similar structures, they are difficult to be distinguished by targeting molecules. As such, false positives and false negatives are inevitable when detecting tumors. Compared with the pharmaceutical disclosed in the Chinese Patent Publication No. CN 109045313A in the same model, the radiopharmaceutical disclosed in the Chinese Patent Publication No. CN 109045313A demonstrated a false positive result in an HER2-negative EGFR-positive MDA-MB-468 breast cancer model and an inferior distinction to that of the pharmaceutical disclosed herein. The radiopharmaceutical of the present invention gave a negative result and better distinction, and will not produce a false positive result due to EGFR expression. Therefore, the radiopharmaceutical has significant advantages in distinguishing tumors with high HER2 and EGFR expressions, showing reduced false positive results.

The invention claimed is:

1. An rk polypeptide radiopharmaceutical targeting HER2, which is $^{99m}$Tc-HYNIC-PKM-(PKM-rk)$_2$, wherein PKM is polyethylene glycol or 8-aminooctanoic acid, and rk is an 8-residue linear polypeptide of D-amino acids with a sequence of Arg-Asn-Trp-Glu-Leu-Arg-Leu-Lys.

2. The rk polypeptide radiopharmaceutical targeting HER2 according to claim 1, which is $^{99m}$Tc-HYNIC-PEG$_4$-(Aoc-rk)$_2$ or $^{99m}$Tc-HYNIC-PEG$_4$-(PEG$_4$-rk)$_2$.

3. The rk polypeptide radiopharmaceutical targeting HER2 according to claim 1, which is $^{99m}$Tc-HYNIC-PKM-(PKM-rk)$_2$, wherein from left to right the first PKM is polyethylene glycol, the second PKM is polyethylene glycol or 8-aminooctanoic acid.

* * * * *